United States Patent [19]

Hanseler

[11] Patent Number: 5,370,713
[45] Date of Patent: Dec. 6, 1994

[54] AUTOMATIC PLANT DIVIDING SYSTEM

[75] Inventor: Kurt Hanseler, Church Point, Australia

[73] Assignee: The Commonwealth Industrial Gases Limited, St. Leonards, Australia

[21] Appl. No.: 877,180
[22] PCT Filed: Sep. 5, 1991
[86] PCT No.: PCT/AU91/00413
 § 371 Date: Jul. 1, 1992
 § 102(e) Date: Jul. 1, 1992
[87] PCT Pub. No.: WO92/03913
 PCT Pub. Date: Mar. 19, 1992

[30] Foreign Application Priority Data
 Sep. 7, 1990 [AU] Australia ............... PK-2193

[51] Int. Cl.5 ............................................. A01G 9/02
[52] U.S. Cl. .................................................. 47/1.01
[58] Field of Search ................................ 47/1.01, 1 A

[56] References Cited

U.S. PATENT DOCUMENTS 4,285,258 8/1981 Logan et al. .

FOREIGN PATENT DOCUMENTS

| | | |
|---|---|---|
| 562086 | 5/1985 | Australia . |
| 0232628 | 8/1987 | European Pat. Off. . |
| 0288873 | 11/1988 | European Pat. Off. ............ 47/1 A |
| 0320995 | 6/1989 | European Pat. Off. . |
| 2512324 | 3/1983 | France ...................... 47/1 A |
| 2579065 | 9/1986 | France ...................... 47/1 R |
| 2610786 | 8/1988 | France ...................... 47/1 A |
| 3195487 | 8/1991 | Japan . |
| 9000803A | 11/1991 | Netherlands .............. 47/1 A |
| 8606576 | 11/1986 | WIPO . |
| 9006058 | 11/1989 | WIPO . |
| 90/10273 | 9/1990 | WIPO ...................... 47/1 T |
| 9201994 | 2/1992 | WIPO . |

Primary Examiner—Thuy M. Bui
Assistant Examiner—Joanne C. Downs
Attorney, Agent, or Firm—Leydig, Voit & Mayer, Ltd.

[57] ABSTRACT

An apparatus (1) for dividing plant materials (4) comprising, a first conveyor (2) to transport a tray (3) or the like so as to selectively position generally upstanding plant material disposed in the tray, harvesting means (7) to grip and sever the plant material (4) adjacent its base when selectively positioned by the first conveyor (2) and to transport the plant material to a dividing station (D), image signal generating and processing means (6) to scan the cutting and cutter means (10) responsive to a division signal from said image signal generating and processing means (6) to divide the plant cutting (5) according to predetermined rules related to the structure of plant material, and planting device (13) to transport and position the divided plant material (17) in a growing medium (20).

29 Claims, 7 Drawing Sheets

AUTOMATIC PLANT DIVIDING SYSTEM

TECHNICAL FIELD

The present invention relates to improvements in the micropropagation of plants and in particular to an apparatus for the dividing of plant materials.

BACKGROUND ART

The advantages of micropropagation are well known. It offers a convenient and effective method of disease control with consequent improvement in plant quality. Freedom from disease is becoming an increasingly important attribute in relation to quarantine retirements imposed in promising export markets such as the Middle East.

Micropropagation provides a method of rapid plant multiplication. In addition to its general significance as a means of achieving dramatic increases in quantity it confers specific benefits. Production of commercial quantities of a new variety can be achieved by a manual micropropagation in approximately 50% of the time required by conventional methods. The facility to rapidly build up numbers of new varieties is important even for species, such as vines, that are easily propagated by cutting.

The micropropagation technique enables the more productive use of space. Subculturing is conducive to the achievement of a pleasingly high rate of utilisation of laboratory space. Better utilisation of glasshouses and plant "hardening" space is also encouraged. Where seasonal markets are being served, rapid multiplication of varieties avoids the necessity to leave unoccupied space in stock houses for protracted periods while numbers are being built up. Operation can be continued at any time of year under controlled conditions of temperature, light cycle and nutrient balance. Culture storage or reduced temperature can be used to reduce growth rate to produce synchronised high output for seasonal demand.

Application of micropropagation to a species requires the identification of a satisfactory relationship between the plant material, culture medium and incubation conditions. The range of species for which a standard procedure for micropropagation has been devised is rapidly increasing with a consequent growth in the potential area in commercial application.

The sequence of operations involved in micropropogation by organ culture is briefly as follows:

(i) Initial culture; shoots are taken from the selected plant, surface sterilised and placed onto a sterile medium.

(ii) The buds on these shoots eventually develop and these are subcultured to shoot multiplication medium (SM).

(iii) The shoots grow rapidly on SM producing a large number of clonal shoots. To increase the number of shoots and to maintain the line, the shoots are subcultured to fresh SM every 3 to 4 weeks.

(iv) Roots develop when a sample of the shoots are subcultured to a rooting medium (RM) in a petri dish or similar container.

The plants are usually dispatched in stacks of containers. The recipient removes them from the containers under non-sterile conditions and "hardens" them to outside conditions in a high humidity environment.

Subculturing is usually performed in a transfer chamber where the shoots are removed from their containers with sterile forceps, dissected, usually quite roughly, with a sterile scalpel into small clumps of shoots or single shoots and then placed onto fresh medium. Pieces cut so as to not contain sufficient whole meristem cells will grow slowly or not at all. Plants containing few or no whole fully differentiated cells are liable to not generate as "true to type" or clonal plants.

The largest cost in the procedure is the labour involved in subculturing the shoots from one medium to another. The cost of subculturing is at least three times the cost of all the other procedures.

The reason for this can be illustrated in terms of the subculturing of trees. Here the performance of 5000 transfer operations per day is an absolute maximum for a technician. Similar productivity constraints apply to these operations whether conducted at macroscopic or microscopic scales. In addition in many laboratories sterility control is incomplete, so that contamination losses can be very substantial. Cleaning, preparation, control and movement of plant containers between cutting, storage and hardening areas and transfers to hardening medium are also very labour intensive.

Due to the intricacy of the handling and cutting operations required and the fragile nature of the plant material, it has been extremely difficult to develop apparatus to assist in these processes which will perform as required without damaging the delicate plant tissues.

Thus, the present ability of the Australian and Overseas nursery industry to satisfy the demand for micro propagated plants is severely constrained by the cost of the manual cutting process and transfer processes presently employed in the micropropogation process and the maximum number of operations per day which may be performed by even the most skilled operator without deleterious side affects.

It is therefore an object of this invention to provide an apparatus for dividing plant materials that will overcome, or at least ameliorate the above disadvantages.

DISCLOSURE OF THE INVENTION

According to the invention there is provided an apparatus for dividing and replanting generally upstanding plant material disposed in a tray, said apparatus comprising conveyor means to position said plant material at a selected harvesting location, harvesting means operable to remove said plant material from said tray and to transport said plant material to a dividing station; imaging means associated with said dividing station to determine locations for the division of said plant material according to predetermined rules related to the plant structure, and cutter means responsive to a division signal from said imaging means to divide the plant material into plant cuttings, and planting means to selectively place said cuttings in a growing medium.

Preferably the conveyor effects a step wise movement of plant material so as to sequentially position rows of plant material growing in the trays. In an embodiment the step wise movement is performed by means of magnetic attraction between an element associated with the tray and a driven element disposed below a low friction conveyor surface.

Preferably the harvesting means grips and severs the plant material adjacent its base. The gripping and severing action is preferably performed by synchronously driven pairs of adjacent gripping fingers and scissor elements. The gripping fingers are preferably in the form of resilient shims.

It is further preferred that the dividing station takes the form of a second conveyor so that the plant material can be moved sequentially for imaging and cutting. The second conveyor is preferably a translucent belt which allows back lighting of the plant material during imaging. The movement of the belt is preferably in discrete steps, each movement corresponding to a spacing between the imaging and dividing stations.

In a preferred embodiment the image signal is generated by a Charge Coupled Device interfaced to a processing means comprising a micro computer. In this case the back lighting ensures good contrast between the plant material and the background thereby assisting operation of the CCD.

More preferably processing means are associated with the imaging means which produces a co-ordinate map of the structure from the image signal and identifies the co-ordinates corresponding to selected features of the structure.

Preferably the cutter means includes two independently operable pairs of opposed gripping fingers disposed either side of a reciprocable cutting blade. This ensures that the plant is held securely during the cutting operation. More preferably, each pair of fingers are pivotally interconnected and include means to bias the fingers toward the open position.

Preferably the planting means comprises a pair of pivotally interconnected gripping fingers including means to bias the fingers into a closed position and selectively operable driving means to open the gripping fingers against the force of the biasing means.

BRIEF DESCRIPTION OF DRAWINGS

A preferred embodiment of the invention will now be described, by way of example only, with reference to the accompanying drawings in which.

BEST MODE OF CARRYING OUT THE INVENTION

Figure 1:
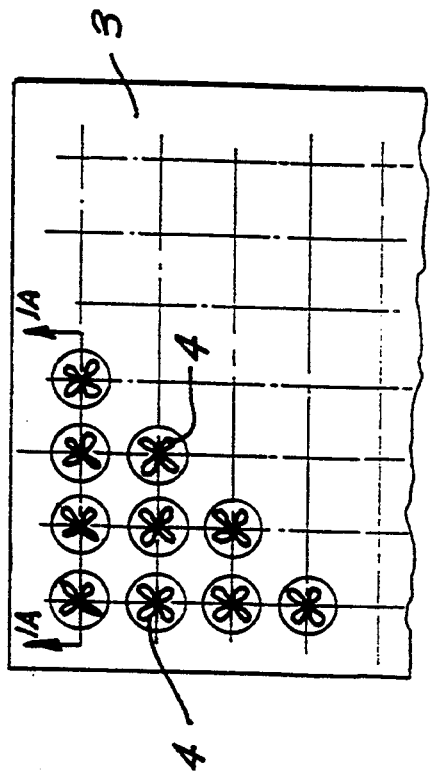
FIG. 1 is a schematic plan view of upstanding plant material to be divided disposed in a tray.
Figure 1A:
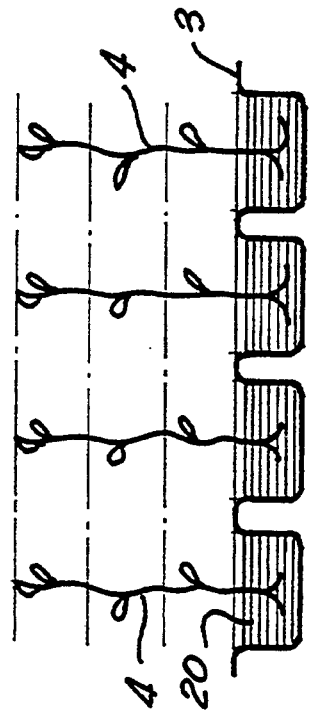
FIG. 1A is a sectional side view of the upstanding plant material to be divided disposed in a tray as illustrated in FIG. 1.
Figure 2:
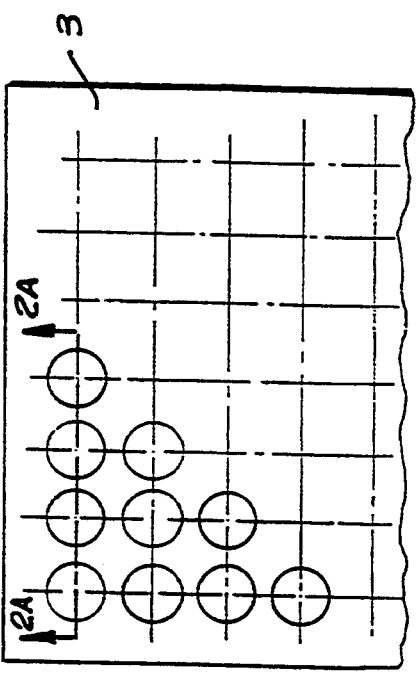
FIG. 2 is a schematic plan view of an empty tray filled with growing medium to which the divided plant cuttings are transferred.
Figure 2A:
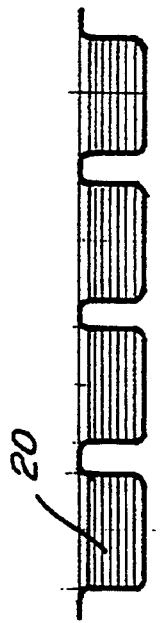
FIG. 2A is a sectional side view of an empty tray filled with growing medium to which the divided plant cuttings are transferred as illustrated in FIG. 2.

Referring to the drawings, the apparatus 1 comprises a conveyor 2 to transport a tray 3 so as to accurately position generally upstanding plant material 4 disposed in the tray.

Located directly above the positioned tray 3 at a location marked A is a reciprocally mounted harvesting means 7 used to grip and sever the plant material 4 adjacent its base and transport the plant cutting 5 to an adjacent second conveyor 6. The harvesting means 7 is mounted on a first slide 8 and is movable between positions indicated approximately by markings A and B.

An imaging means in the form of a Charged Coupled Device (CCD) 9 is disposed directly above the second conveyor 6 at a point longitudinally down stream of the harvesting means at a position marked C.

Directly downstream of the CCD 9 is a cutter 10, similarly incorporating its own gripping mechanism. The cutter means 10 is slidably mounted on a second slide 12 and is reciprocally movable between positions indicated generally at D and E. Positions B, C and D generally denote the dividing station.

Immediately downstream from position E above the first conveyor is a planting device 13. The planting device 13 is similarly slidably mounted on a third slide 14 and is reciprocally movable between positions marked F and G.

Figure 3:
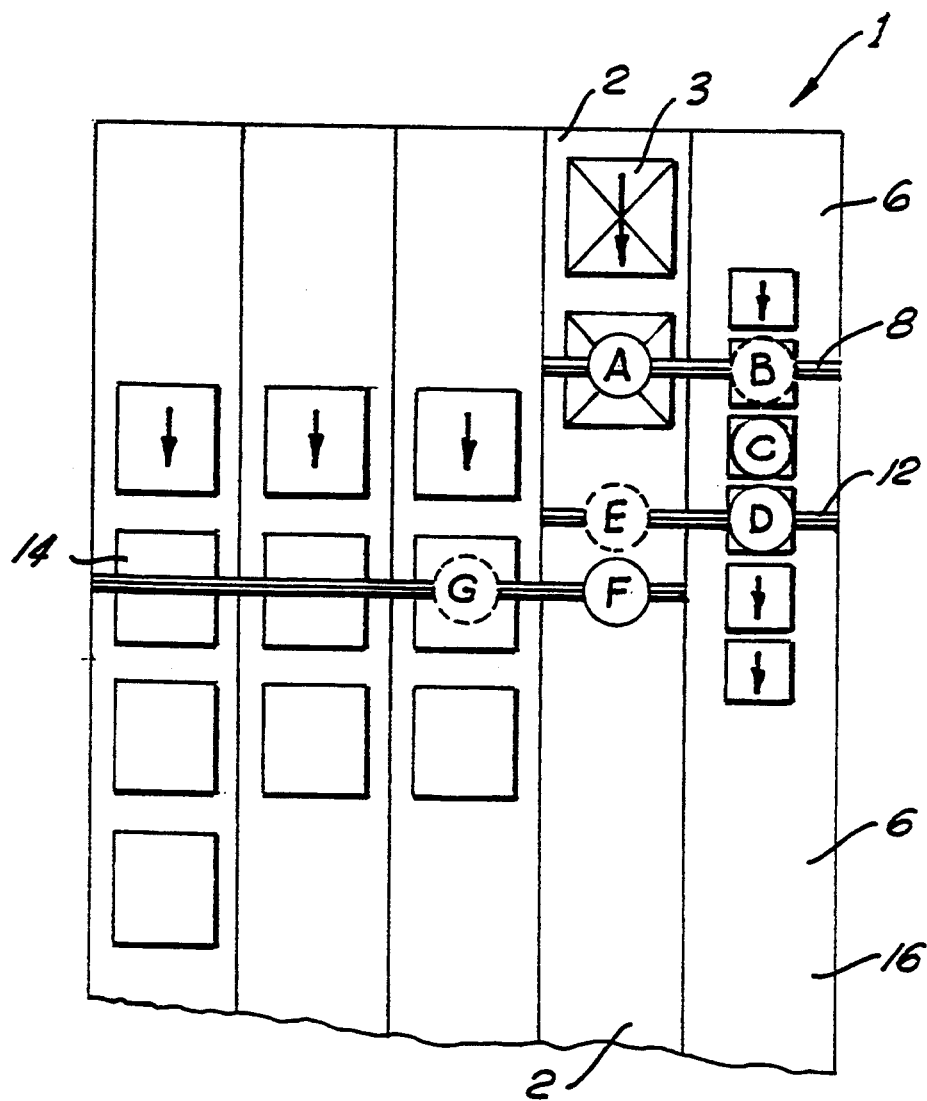
FIG. 3 is a schematic layout of the apparatus illustrating the main sequence of operation according to the invention.
Figure 4:
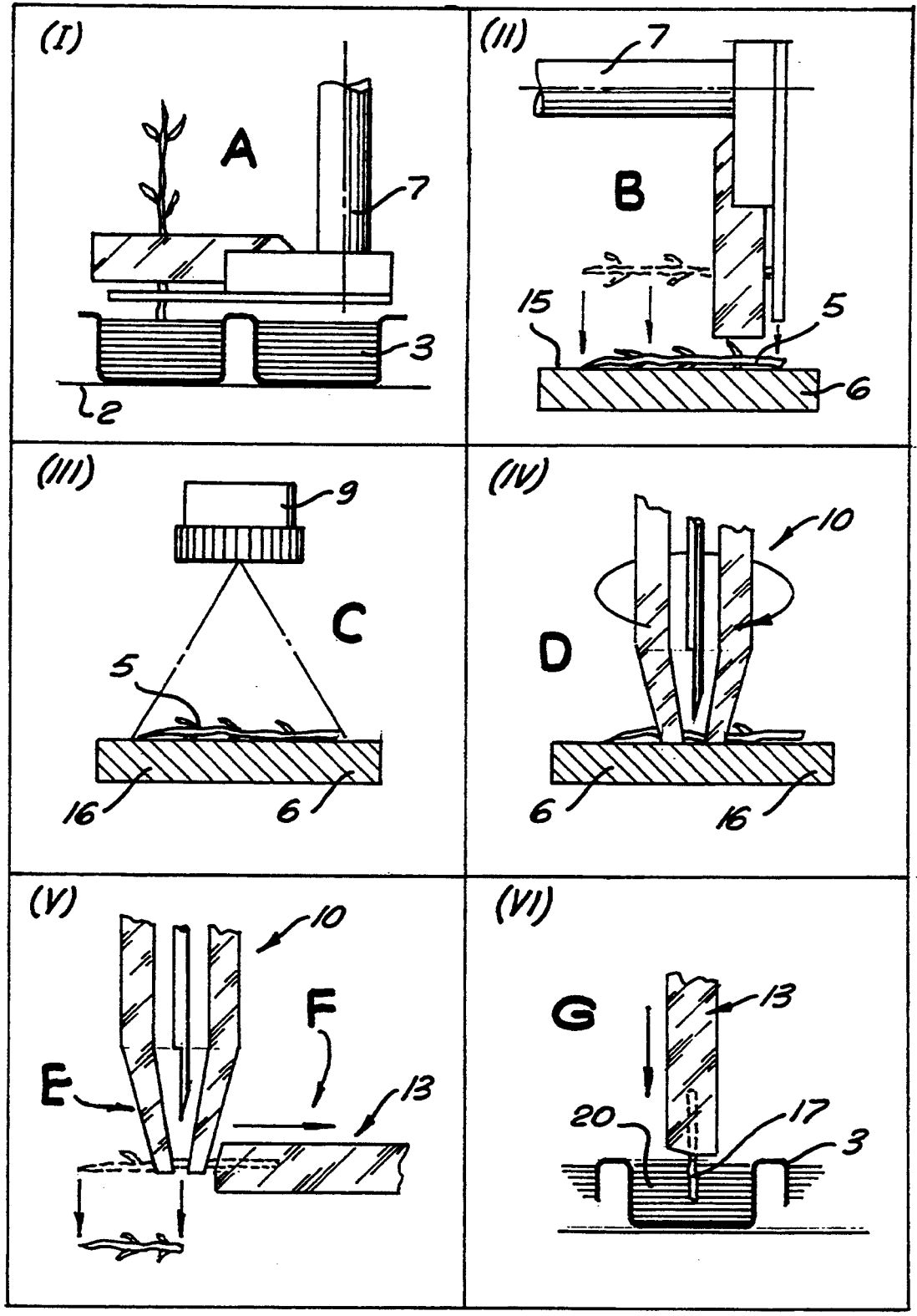
FIG. 4 is a schematic representation of the various stages and elements of the apparatus according to the invention.

Referring now in particular to FIG. 3 and FIG. 4, the sequence of operation of the apparatus will be described in general terms.

The tray 3 of upstanding plant material 4 is indexed into the unloading position at position A directly beneath the harvesting device 7. The device 7 is pivotally mounted and swings down through an accurate path to engage with the plant material as shown in part (i) of FIG. 4. By translation and rotation of the harvesting device 7 from position A to position B, the plant material 4 is transferred onto the second conveyor 6 as illustrated in part (ii) of the drawing.

In this embodiment the second conveyor 6 comprises a continuous length of clear plastic film 15 extending over a light table 16. The plant is then indexed from position B to position C by indexing the film 15 in discreet steps by means of a reciprocating pneumatic cylinder (not shown).

The plant material 4 is then scanned by the CCD camera 9. Details of the apparatus forming part of the camera system have not been shown, but are incorporated herein by reference to Australian Patent No. 591,678.

The CCD captures an image of the plant and its branch nodes and the micro computer processes that information to provide instructions to the cutter means provided at location D, to divide the plant cutting 5 according to predetermined rules related to the structure of plant materials.

After indexing the cutting 5 to position D, the cutter 10 first grips the plant material then divides it at the predetermined location, transporting the tip cutting 17 of the plant to position E by translation of the cutting device 10 along the second slide 12. At this point the tip cutting 17 is transferred to the planting means 13 which translates and rotates the plant segments through 90° for planting in the growing medium 20.

Figure 5:
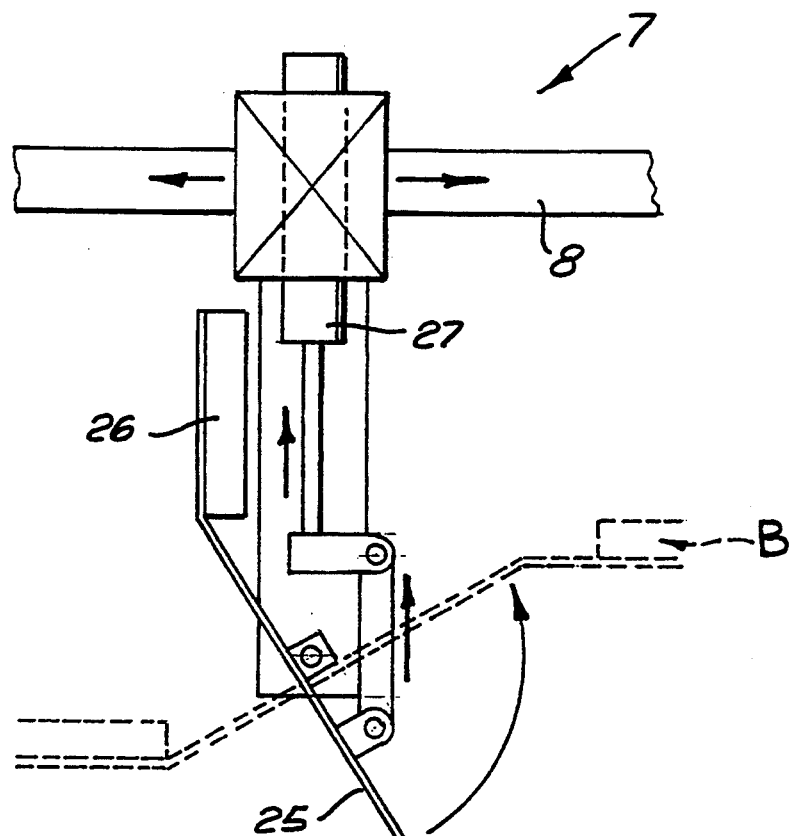
FIG. 5 is a schematic side view of one embodiment of a harvesting means according to the invention.
Figure 6:
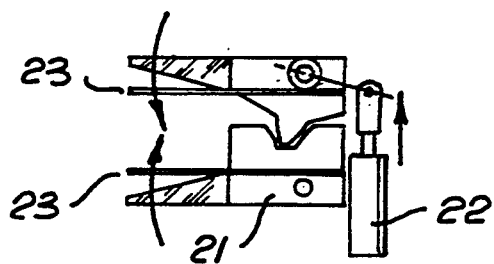
FIG. 6 is a schematic plan view of the jaws forming part of the harvesting means shown in FIG. 5.

Referring now in particular to FIGS. 5 and 6, the harvesting device 7 comprises a pair of drivingly interconnected scissor elements 21 operable by a small reciprocating pneumatic cylinder 22. Connected with each scissor element 21 is a resilient clamping shim 23 positioned such that during closing of the scissors 21 the shims 23 will engage prior to engagement of the scissor elements 21. In this way, the plant material is gripped securely prior to cutting.

The cutting jaws are supported from the first slide 8 by means of a pivoting arm 25 having at its free arm a counter weight 26. The arm 25 is connected at a point spaced apart from the pivoting point to a reciprocating pneumatic cylinder 27 which enables movement of the cutters between the orientations shown, from the vertical mode required when in use at position A to the horizontal mode required when in use at position B.

Figure 7:
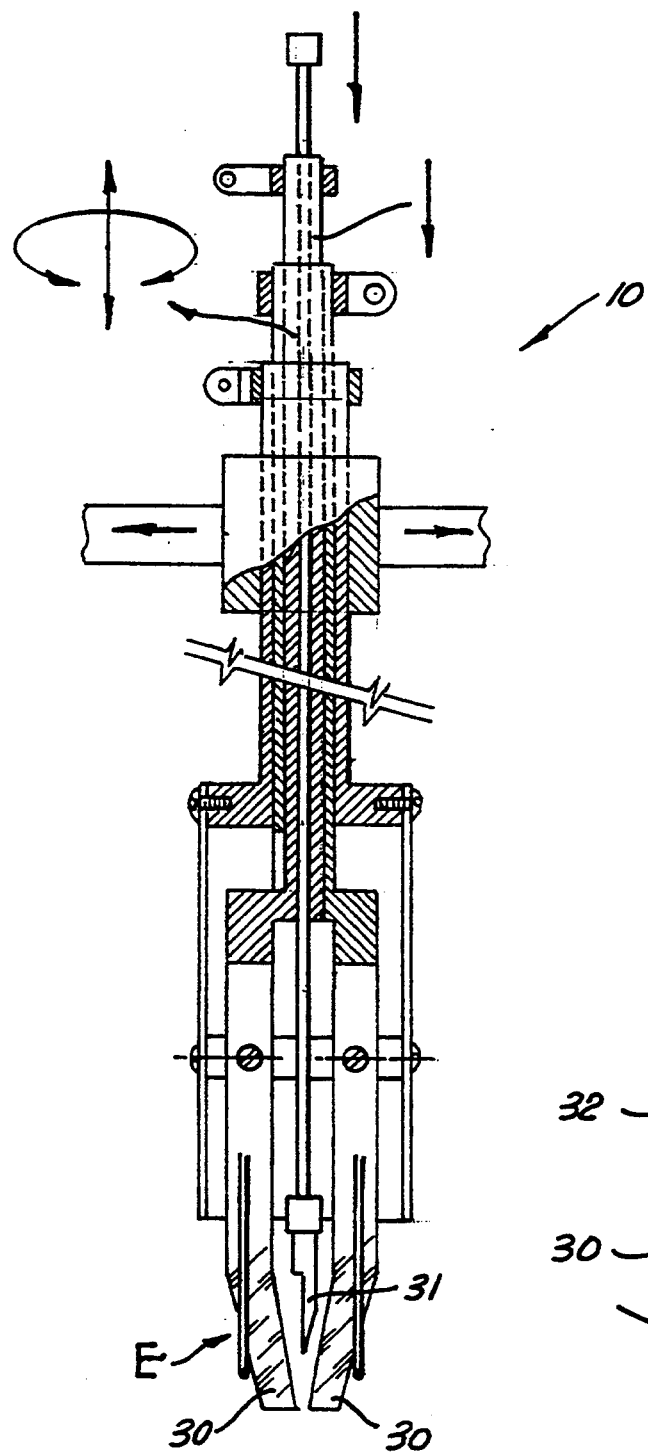
FIG. 7 is a schematic part sectioned side view of a cutter means according to the invention.
Figure 8:
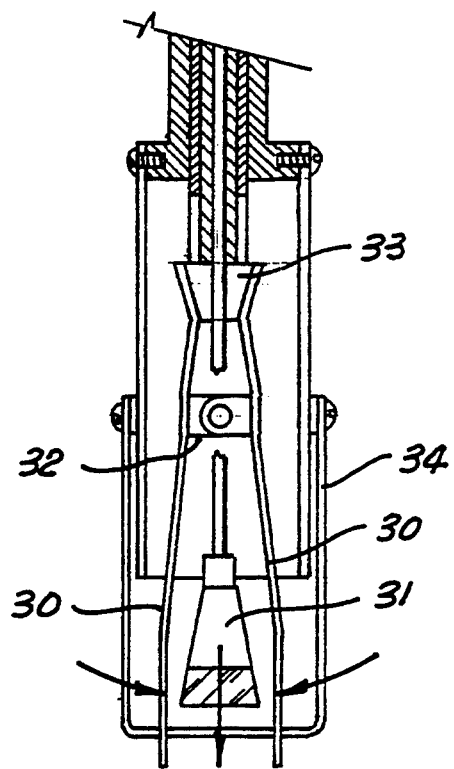
FIG. 8 is a schematic sectioned view of part of the cutter means shown in FIG. 7.

Referring now to FIGS. 7 and 8, the cutter 10 comprises essentially two independently operable pairs of gripping fingers in the form of shims 30 disposed either side of a reciprocating cutting blade 31 each operable by a pneumatic cylinder. Each pair of gripping shims are pivotally interconnected part way along their length having therebetween a spring 32 that biases the working ends of the shims into an open position. Two restraining loops 34 are provided to prevent the plant cutting 5 from tilting out of a horizontal plane during cutting.

A reciprocally movable tapered ram 33 is disposed between one end of the shims 30 which in use can be lowered by a pneumatic cylinder to force that end of the shims apart against the biasing force of the spring 32 thereby causing the working end of the shims to move together into gripping engagement. Each pair of shims are independently operably by respective pneumatic cylinders.

The device 10 is supported from the second main slide 12 via a cross slide with vertical drive and rotation device not shown. This enables accurate spatial positioning of the cutting device 10 according to the instructions received from the micro computer.

Figures 9, 10:
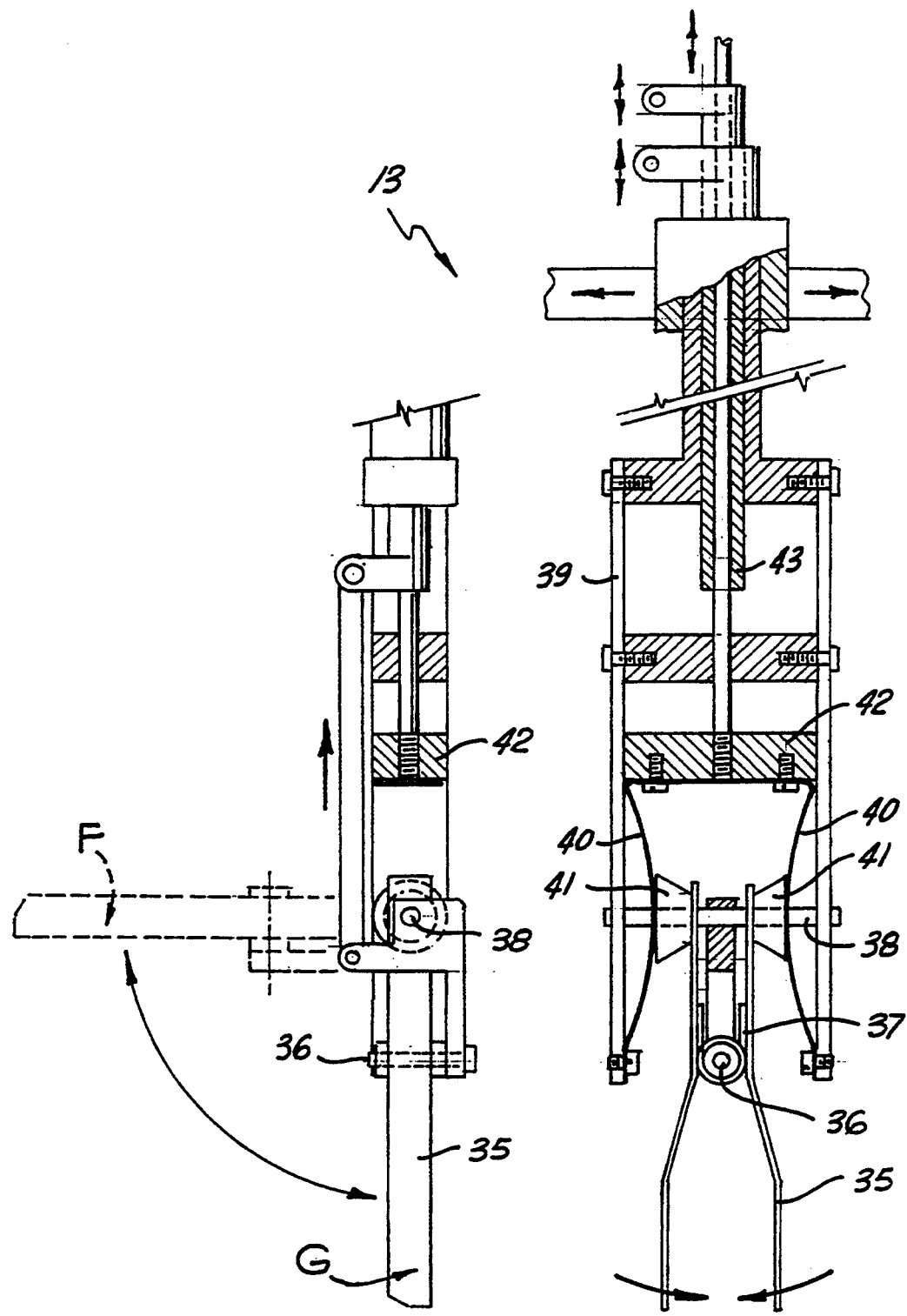
FIG. 9 is a schematic sectioned view of part of a planting means according to the invention.
FIG. 10 is a schematic end view of the device shown in FIG. 9.

Referring specifically to FIGS. 9 and 10, there is shown the planting means 13 according to the invention. The device 13 comprises a single pair of resilient gripping shims 35 pivotally interconnected at a point 36 at which there is provided a spring 37 which urges the captive end of the shims away from each other, thereby biasing the gripping end of the shims toward mutual engagement.

The shims 35 are supported from a rod 38 secured to a main frame 39 which in turn is mounted with the third slide 14. Rigidly connected to the frame 39 is a substantially 'U' shaped leaf spring 40, its two parallel sides connected with the upper ends of the gripping shims 35 by means of conical shaped spacers 41. The length of the leaf spring intermediate these two sides is connected to a reciprocating cross beam 42 that is movable toward and away from the gripping shims 35 to selectively deform the sides of the spring 40 and force the gripping shims against the bias of the spring 37 into the open position.

The gripping shims 35 are pivotable about the rod 38 by means of a pneumatic cylinder 43 enabling movement of the shims between a horizontal and vertical mode as shown in FIG. 9. The device 13 is supported from the third slide 14.

Referring in more detail to the construction and operation of the image generating device, the CCD 9 is a Mintron CCD camera connected to a camera control unit (CCU). The CCD 9 is connected via the CCU to a PC vision plus frame grabber board to a Zenith computer. A signal representative of the structure of the plant cutting 5 positioned on the continuous belt or film 15 and scanned by the CCD 9 is captured by the CCD camera and the signal is digitised before being down loaded onto the main memory of the microcomputer. The plant is scanned against a background of contrasting colour (provided in this case by the light table) and scanning of the plant cutting 5 by the CCD 9 is controlled by the microcomputer. In this way the CCD 9 is actuated to provide a single image of the plant cutting 5.

The digitized signal stored in the micro computer is a representative of a two tone image of the plant in a two dimensional pixel array of 640 pixels horizontal and 400 pixels vertically. The tone assigned to each pixel corresponds to either background or plant. The digitised image signal is processed by systematically determining the tone assigned to each pixel in the array and recording the co-ordinates of plant tones in a data base to form a co-ordinate map.

In addition co-ordinates corresponding to the tips of branches and nodes where branches join are identified and stored in a data base. Systematic processing of each pixel in the array is conducted twice, once using a Down Scan routine and once using an Up Scan routine. The Down Scan and Up Scan routines process the pixel sequentially in different directions and the co-ordinates representing branch tips and nodes obtained by each routine are averaged.

The first step in the Process pixel routine is a back scan for an upwardly sloping branch. This is required because the same branch identifying technique used in the Process pixel routine is based on determining whether background or branch is represented by the pixel to left, the pixel above and to the left and the pixel immediately above the pixel being processed. A branch sloping upwardly to the left can therefore initially be identified as a new branch until a pixel immediately above the pixel being processed is discovered to be a pixel representing plant. When this is determined the back scan is implemented to reliable plant pixels immediately to the left as being in the same branch as the plant pixel identified immediately above the pixel being processed.

Figure 11:
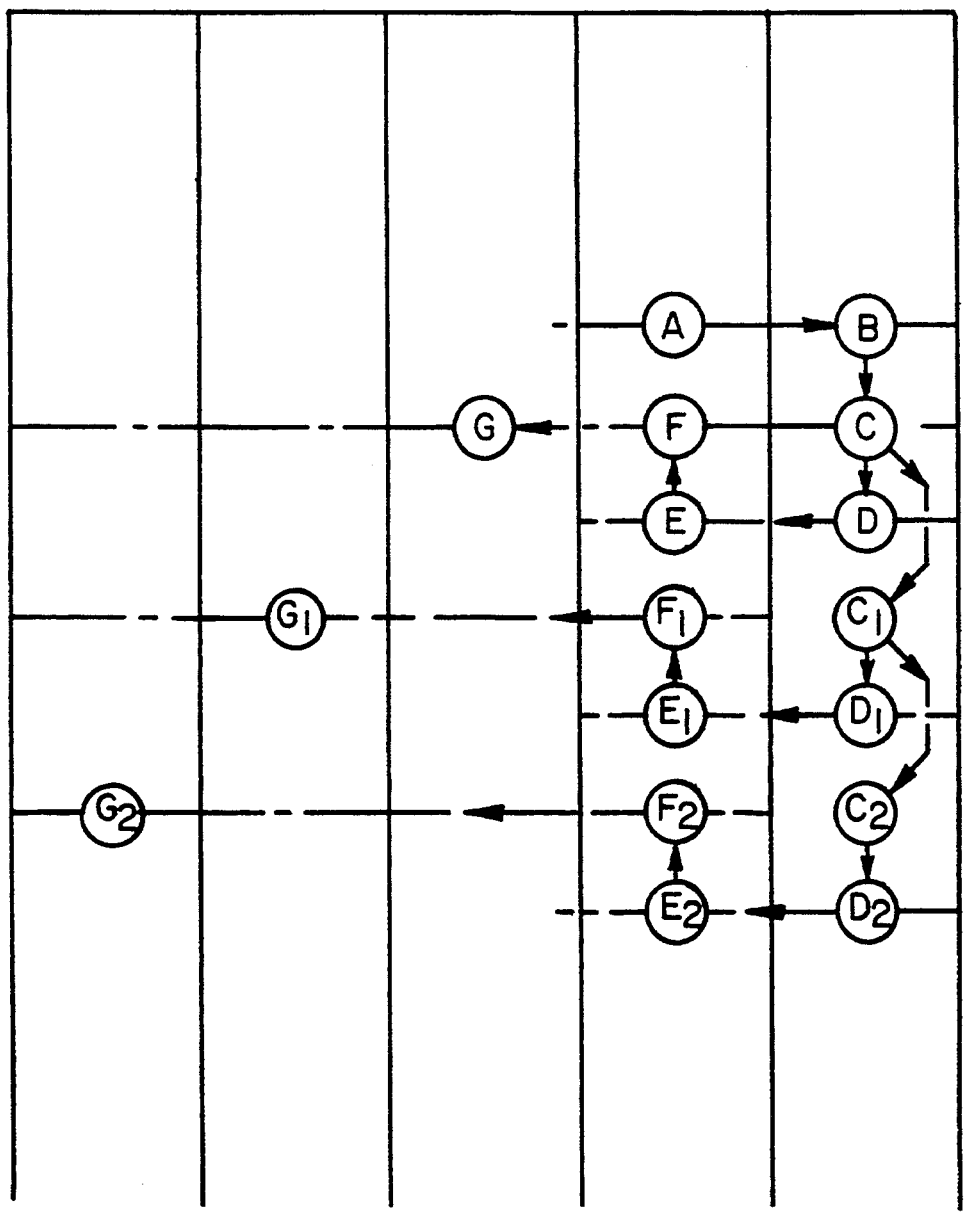
FIG. 11 is a schematic layout illustrating a preferred sequence of operations of the apparatus according to the invention.

Referring finally to FIG. 11 there is shown a complete schematic layout of the apparatus according to the invention which comprises three consecutive stages of apparatus previously described.

In summary, the plant material enters the apparatus in trays as shown in FIG. 1 which are indexed by means described later, until the first row of the tray is directly beneath the centre line position indicated at the position marked A. At this point the harvesting device 7 traverses in the direction from position B to the location of the plant in the first row closest to the second conveyor 6. The device 7 is moved in the horizontal position and swung down through an arcuate path to encompass the first plant. The gripping shims 23 of the harvesting device 7 then grasps the plant 4 and the scissor elements 21 sever the stem adjacent its base.

The harvesting device 7, still gripping the plant, is then swung into the horizontal mode and traversed over to the second conveyor 6 where the plant is released at B. The conveyor 6 then indexes the plant cutting 5 in a stepwise motion to the location marked at C where the plant is scanned by the CCD. Processing of the scanning data will result in the instructions being directed to the cutter 10 at D so that when the plant cutting 5 is indexed the cutter will divide the plant at a specially selected predetermined location.

When the plant cutting 5 is in position at D the cutter 10 is positioned over the plant in accordance with the signal from the micro computer. The cutter is then lowered with the pairs of gripping shims in the open position astride the stem of the plant. When the device is in the fully lowered position the gripping shim pneumatic cylinders are actuated and both pairs of grippers are closed around the stem of the plant and the reciprocating cutter actuated. The two wire restraining loops 34 prevent the plant deforming upwards from the table keeping it substantially parallel to the surface of the light table.

On completion of the cutting operation the pair of gripping shims holding the longest portion of plant material are released and the pair of shims holding the selected tip cutting 17 of plant material remain closed. The cutter 10 is then raised from the table with the cutting 17 and traversed to the position shown at E. From position E the cutting 17 is released from the cutter gripper and transferred to the planting device 13 located at position F, The transfer takes place with the planting device gripping shims in the horizontal position. This device 13 then traverses to position G and the gripping shims are rotated into the vertical position and the cutting 17 is lowered into the growing medium at G.

Whilst the transfer and planting operations of the cutting are being performed the remaining portion of the plant material at D is indexed along the second conveyor 6 to a second CCD located at position C1 at which the sequence begins again resulting in a second cutting being planted at G1, Similarly, the cycle is repeated with the remaining plant material and a third cutting planted at location G2, Thereby positions C1 and D1 respondent a second division station.

Whilst the subsequent operations are being performed on the first plant cutting 5, the harvesting device returns to the infeed tray 3 indexing along the row to the next plant and repeats the sequence. When one row has been exhausted the tray indexes forward on the first conveyor and the next row is processed.

In one embodiment the indexing of the trays both for the infeed or first conveyor and for the trays in which the cuttings are planted is in the form of support surface under which traverses one or more magnets. The trays are then supported on metallic holders which are capable of being magnetised and thus of being located by movement of the magnets. The magnets are driven by any suitable means including for example along a toothed beam by a geared stepper motor.

The main advantage of using this or any other form of remotely operated conveyor system is that sterile conditions can therefore be maintained in a sealed environment above the support surface, minimizing the risks of loss through contamination.

The resulting system is extremely fast, clean and reliable and the design of the gripping devices ensures the delicate plant tissue is not damaged.

Depending on the type of plant material to be divided, alternate embodiments incorporate additional stages at which the side shoots or leaves of the plant cutting are trimmed.

Although the invention has been described with reference to specific examples it will be appreciated by those skilled in the art that the invention may be embodied in many other forms.

I claim:

1. An apparatus for dividing and replanting generally upstanding plant material disposed in a tray, said apparatus comprising:
   conveyor means to position said plant material at a selected harvesting location;
   harvesting means to remove said plant material from said tray and to transport said plant material to a dividing station, said harvesting means comprising synchronously driven pairs of adjacent gripping fingers and scissor elements which remove said plant material from said tray by gripping said plant material with said gripping fingers and severing said plant material with said scissor elements;
   imaging means associated with said dividing station to determine locations for the division of said plant material according to predetermined rules related to the plant structure;
   cutter means responsive to a division signal from said imaging means to divide the plant material into plant cuttings, and;
   planting means to selectively place said cuttings in a growing medium.

2. An apparatus according to claim 1 wherein said conveyor means includes a magnetic coupling formed between a magnet associated with the tray and a driven magnet located below a low friction surface of the conveyor.

3. An apparatus according to claim 1 wherein the conveyor means effects a step wise movement of plant material so as to sequentially position row of plant material at said harvesting location.

4. An apparatus according to claim 1 wherein said gripping fingers grip and said scissor elements sever said plant material adjacent the base of said plant material.

5. An apparatus according to claim 1 wherein the gripping fingers are resilient shims.

6. An apparatus according to claim 1 wherein the dividing station includes a second conveyor for sequentially moving the plant material to locations for imaging and cutting operations.

7. An apparatus according to claim 6 wherein the second conveyor is comprised of a translucent material which allows back lighting of the plant material during imaging.

8. An apparatus according to claim 7 wherein the movement of the second conveyor is in discrete steps, each movement corresponding to a spacing between the imaging and dividing stations.

9. An apparatus according to claim 6 wherein the movement of the second conveyor is in discrete steps, each movement corresponding to a spacing between the imaging and dividing stations.

10. An apparatus according to claim 1 wherein the imaging means is a Charge Coupled Device interfaced to a processing means for producing a image signal representative of an image of said plant material.

11. An apparatus according to claim 10 wherein the processing means associated with the imaging means produces a co-ordinate map of the structure from the image signal and identifies the co-ordinates corresponding to selected features of the structure.

12. An apparatus according to claim 1 wherein the cutter means includes two independently operable pairs of opposed gripping fingers disposed on either side of a reciprocable cutting blade.

13. An apparatus according to claim 1 wherein the planting means comprises a pair of pivotally interconnected gripping fingers including means to bias the fingers into a closed position and selectively operable driving means to open the gripping fingers against the force of the biasing means.

14. A method of dividing and replanting generally upstanding plant material disposed in a tray, comprising the steps of:
removing said plant material from said tray using harvesting means comprising synchronously driven pairs of adjacent gripping fingers and scissor elements which remove said plant material from said tray by gripping said plant material with said gripping fingers and severing said plant material with said scissor elements;
forming an image of said plant material;
producing an image signal representative of said image;
determining from said image signal, locations for the division of said plant material according to predetermined rules related to the plant structure;
dividing the plant material into plant cuttings by cutting at said determined locations; and
planting said cuttings in a growing medium.

15. A method according to claim 14, wherein the plant material is divided into cuttings using two independently operable pairs of opposed gripping fingers disposed on either side of a reciprocable cutting blade.

16. An apparatus for dividing and replanting generally upstanding plant material disposed in a tray, said apparatus comprising:
conveyor means to position said plant material at a selected harvesting location, said conveyor means including a magnetic coupling formed between a magnet associated with the tray and a driven magnet located below a low friction surface of the conveyor;
harvesting means to remove said plant material from said tray and to transport said plant material to a dividing station;
imaging means associated with said dividing station to determine locations for the division of said plant material according to predetermined rules related to the plant structure;
cutter means responsive to a division signal from said imaging means to divide the plant material into plant cuttings, and;
planting means to selectively place said cuttings in a growing medium.

17. An apparatus according to claim 16 wherein the conveyor means effects a step wise movement of plant material so as to sequentially position rows of plant material at said harvesting location.

18. An apparatus for dividing and replanting generally upstanding plant material disposed in a tray, said apparatus comprising:
conveyor means to position said plant material at a selected harvesting location;
harvesting means to remove said plant material from said tray and to transport said plant material to a dividing station;
imaging means associated with said dividing station to determine locations for the division of said plant material according to predetermined rules related to the plant structure;
cutter means responsive to a division signal from said imaging means to divide the plant material into plant cuttings, said cutter means comprising two independently operable pairs of opposed gripping fingers disposed on either side of a reciprocable cutting blade, and;
planting means to selectively place said cuttings in a growing medium.

19. An apparatus according to claim 18 wherein said conveyor means includes a magnetic coupling formed between a magnet associated with the tray and a driven magnet located below a low friction surface of the conveyor.

20. An apparatus according to claim 18 wherein the conveyor means effects a step wise movement of plant material so as to sequentially position row of plant material at said harvesting location.

21. An apparatus according to claim 18 wherein the dividing station includes a second conveyor for sequentially moving the plant material to locations for imaging and cutting operations.

22. An apparatus according to claim 21 wherein the second conveyor comprises a translucent material which allows back lighting of the plant material during imaging.

23. An apparatus according to claim 21 wherein the movement of the second conveyor is in discrete steps, each movement corresponding to a spacing between the imaging and dividing stations.

24. An apparatus according to claim 18 wherein the imaging means is a Charge Coupled Device interfaced to a processing means for producing an image signal representative of an image of said plant material.

25. An apparatus according to claim 24 wherein the processing means associated with the imaging means produces a co-ordinate map of the structure from the image signal and identifies the co-ordinates corresponding to selected features of the structure.

26. An apparatus according to claim 18 wherein each pair of opposed gripping fingers are pivotally interconnected and include means to bias the fingers toward the open position.

27. An apparatus according to claim 18 wherein the planting means comprises a pair of pivotally interconnected gripping fingers including means to bias the fingers into a closed position and selectively operable driving means to open the gripping fingers against the force of the biasing means.

28. An apparatus according to claim 18 wherein each pair of opposing gripping fingers are pivotally interconnected and include means to bias the fingers toward the open position.

29. An apparatus for dividing and replanting generally upstanding plant material disposed in a tray, said apparatus comprising:
conveyor means to position said plant material at a selected harvesting location;
harvesting means to remove said plant material from said tray and to transport said plant material to a dividing station;
imaging means associated with said dividing station to determine locations for the division of said plant material according to predetermined rules related to the plant structure;
cutter means responsive to a division signal from said imaging means to divide the plant material into plant cuttings, and;
planting means to selectively place said cuttings in a growing medium, said planting means comprising a pair of pivotally interconnected gripping fingers including means to bias the fingers into a closed position and selectively operable driving means to open the gripping fingers against the force of the biasing means.

* * * * *

UNITED STATES PATENT AND TRADEMARK OFFICE
CERTIFICATE OF CORRECTION

PATENT NO. : 5,370,713
DATED : December 6, 1994
INVENTOR(S) : Kurt Hanseler

It is certified that error appears in the above-indentified patent and that said Letters Patent is hereby corrected as shown below:

Column 7, line 23, delete "F," and substitute therefor -- F. --;

Column 7, line 33, delete "G1," and substitute therefor -- G1. --; and

Column 7, line 35, delete "G2," and substitute therefor -- G2. --.

IN THE CLAIMS:

Column 8, line 55, delete "a" and substitute therefor -- an --; and

Column 10, line 10, delete "row" and substitute therefor -- rows --.

Signed and Sealed this

Seventeenth Day of October, 1995

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,370,713
DATED : DECEMBER 6, 1994
INVENTOR(S) : KURT HANSELER

It is certified that error appears in the above-indentified patent and that said Letters Patent is hereby corrected as shown below:

ON THE TITLE PAGE:

[73] ASSIGNEE: delete "The Commonwealth Industrial Gases Limited, St. Leonards, Australia" and substitute therefor -- Queensland Science and Technology Limited, Brisbane, Australia --;

Signed and Sealed this

Twenty-third Day of January, 1996

Attest:

BRUCE LEHMAN

*Attesting Officer*  *Commissioner of Patents and Trademarks*